United States Patent [19]

Farfan de los Godos

[11] Patent Number: 4,691,696
[45] Date of Patent: Sep. 8, 1987

[54] LUMBAR SPINAL BRACE

[75] Inventor: Henry F. Farfan de los Godos, Beebe, Canada

[73] Assignee: 102160 Canada Inc., Beebe, Canada

[21] Appl. No.: 697,400

[22] Filed: Feb. 1, 1985

[51] Int. Cl.$^4$ ............................................. A61F 5/02
[52] U.S. Cl. ..................................... 128/78; 128/95.1
[58] Field of Search ................... 128/77, 95, 99, 102, 128/78; 2/44

[56] References Cited

U.S. PATENT DOCUMENTS

| | | | |
|---|---|---|---|
| 1,650,650 | 11/1927 | Pieper | 128/78 |
| 2,687,129 | 8/1954 | Talkish | 128/78 |
| 3,029,810 | 4/1962 | Martin | 128/78 |
| 3,351,053 | 11/1967 | Stuttle | 128/78 |
| 3,878,841 | 4/1975 | Villanvena | 128/78 |

Primary Examiner—Robert Peshock
Assistant Examiner—John G. Weiss

[57] ABSTRACT

A lumbar spinal brace comprises a belt adaptable to be wrapped into a generally round shape having left and right hand halves and a central axis dividing said halves, a first bracing structure extending from the belt, a contact point defined by the first bracing structure, said contact point being disposed upwardly and laterally from the central axis, the first bracing structure being resistant to rearward movement of the contact point, and, said first bracing structure comprising a support member extending from the belt and having an upper portion defining the contact point, and, a movement limiting structure connected to the support member and the belt for resisting rearward movement of the contact point.

31 Claims, 5 Drawing Figures

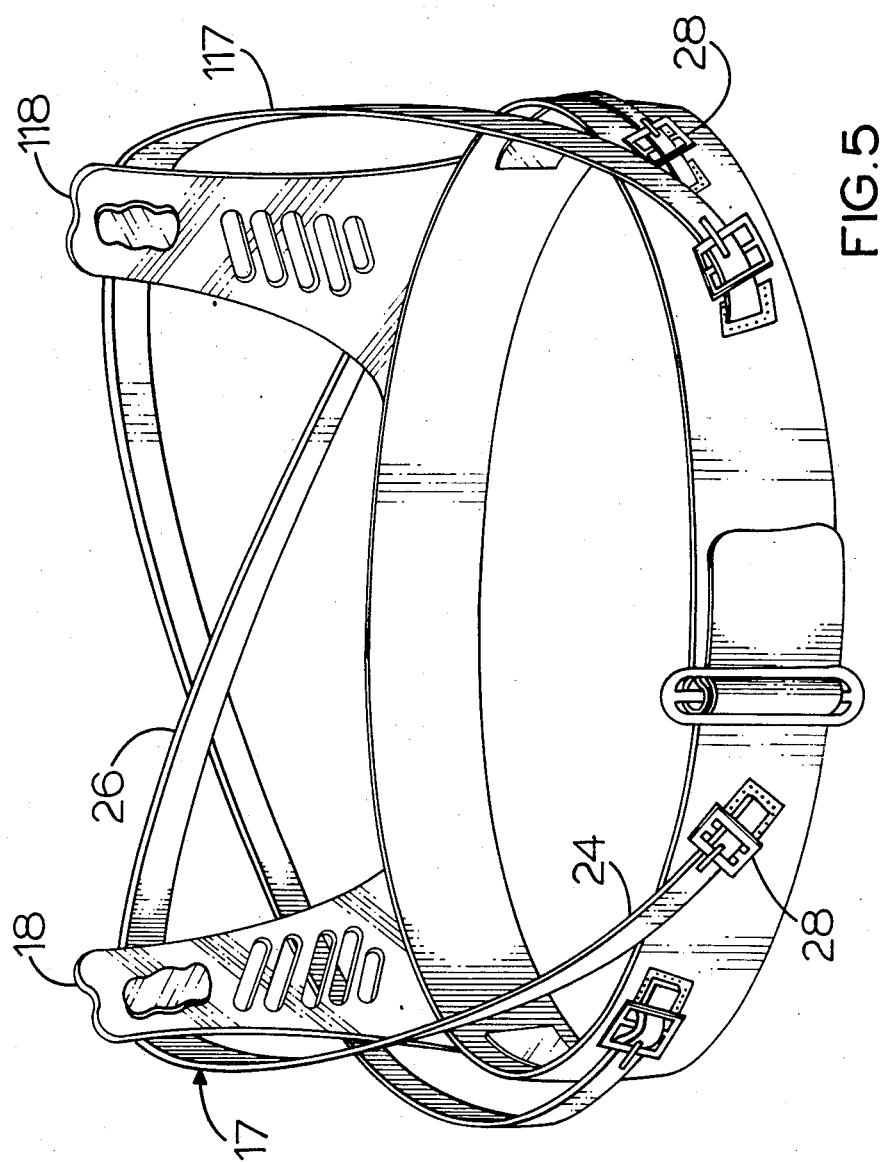

LUMBAR SPINAL BRACE

NATURE OF THE INVENTION

The invention relates to a brace for supporting the lumbar spine. In particular, the invention relates to a brace that is resistant to torsion in at least one rotational direction.

BACKGROUND OF THE INVENTION

The human spine is an essential load bearing component in the human skeleton. Damage to the spine may render the injured person uncomfortable, disabled or incapacitated, Any injury to the spine will likely cause at least some discomfort, immobility or pain. After an injury to the spine has occurred, it is critical that the spine be given an opportunity to heal itself. Spinal motion in the direction of the injury must be avoided if the injury is not to be aggravated. If no such opportunity to heal is allowed, an injury may never heal. The victim may thus become subject to chronic discomfort, immobility, pain and incapacity. However, because the spine is in constant everyday use, it is continuously subjected to stress which may interfere with the healing process. Accordingly, any device, which will allow everyday use and yet will also provide some protection to the spine as it is healing, would be advantageous.

Spinal injuries are common. Statistics indicate that about one in every four adults suffers at some point from back or back-related problems. Many injuries of the spine occur in the lumbar region of the spine. In common everday activities, such as lifting, sports, extended sitting, and at work, the lumbar spine is exposed to stress, and consequently to injury or re-injury. In certain activities, particularly occupational activities, stress, including torsional stress, may be repeatedly applied to the spine.

The lumbar spine can be injured in essentially two ways—namely, excessive compression or excessive torsion. If the former occurs, the most common result is a damaged vertebral endplate. The lumbar spine is relatively resistant to compression injury. The remedy is preferably rest. Corrective surgery is rarely required.

If excessive torsion or twising occurs, the most common result is a damaged intervertebral disc. In extreme cases, the nucleus of an injured disc may rupture the annulus of the disc and protrude therethrough. Such a protruded disc, or "slipped disc" as it may colloquially be called, may pinch the spinal nerves causing extreme leg pain, or even paresis or paralysis. Corrective surgery to remove disc protrusions or even entire discs may be required. A series of reltaively minor torsional injuries if not allowed to heal may result in a significantly weakened disc, whicy may be susceptible to more serious injury. The lumbar spine is more susceptible to injury by torsion than by compression. Continued twisting toward an injured side may aggravate the injury and interfere with the healing process.

Accordingly, any device which can be used to assist in the preventing or healing of a torsional injury would be valuable. Such a device would also be useful to assist in recuperation after corrective surgery. A device, for instance, which could prevent twisting toward a side which has already been injured would be useful. As well, a device which could reduce the risk of torsional injury would be advantageous. For example, a person exposed to repeated torsional stress, say in an occupational activity, could wear the device in order to protect himself from injury.

Commonly, various braces are used to support the lumbar spine after it has been injured. Several well known braces are of the wrap-around corset type. Such corset braces wrap around the trunk of the body in the region of the lumbar spine. Such braces, however, are intended to reduce the compressive stress on the lumbar spine or to totally immobilize it. They are thus of limited value in the treatment of torsional injuries. In addition, they may be uncomfortable and ill-fitting to larger persons.

Rigidly reinforced or rigid frame back braces are also well known. Such braces however completely immobilize the entire spine. A patient using such a brace is rendered essentially disabled because he cannot move his spine in any way.

It would be advantageous therefore if a brace could be provided that was specifically directed to torsional injuries. Such a brace would prevent torsion, or twisting, of the lumbar spine in the rotational direction in which the spine was originally injured or in which it may be likely to be injured. Preferably, the brace would allow movement in all other directions including extension, flexion and twisting in the uninjured direction. Such a brace would resist dangerous twisting during dangerous activity or healing, but also allow for maximum mobility. In addition, the brace should be as comfortable as possible for persons with different physiques.

STATEMENT OF THE INVENTION

With a view to overcoming the foregoing problems and to providing the above advantages, the invention comprises a lumbar spinal brace comprising a belt adaptable to be wrapped into a generally round shape having a left and right hand halves and a central axis dividing said halves, a first bracing means extending from the belt, a contact point defined by the first bracing means, said contact point being disposed upwardly and laterally from the central axis, the first bracing means being resistant to rearward movement of the contact point the first bracing means comprising a support member extending from the belt and having an upper portion defining the contact point, and, a movement limiting means connected to the support member and the belt for resisting rearward movement of the contact point.

The invention achieves the following advantages. If the upper torso attempts to turn in the same direction as the injury (or in the direction of the potential injury), the back of the patient at his lower ribs will contact the bracing means at the contact point. The bracing means resists backward movement of the contact point and thus resists further rotation in that direction. Accordingly, the injury cannot occur, or it cannot be aggravated. It is thus given a better opportunity to heal. On the other hand, if the upper torso turns in the opposite direction to the injury, the brace is inactive. Mobility in the uninjured direction is improved. Full spinal flexion and some extension are also allowed. In addition, the lumbar spinal brace according to the invention is also relatively comfortable and convenient to use by persons of most physiques.

The various features of novelty which characterize the invention are pointed out with particularity in the claims annexed to and forming a part of this disclosure. For a better understanding of the invention, its operating advantages and specific objects attained by its use,

IN THE FIGURES

DESCRIPTION OF A SPECIFIC EMBODIMENT

Figure 1:
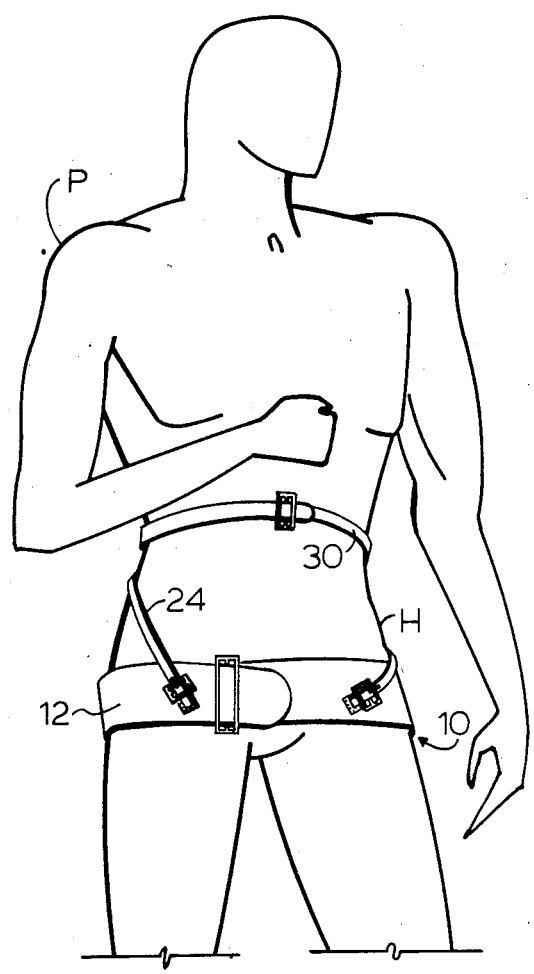
FIG. 1 is a front view of a patient using a brace according to the invention.
Figure 2:
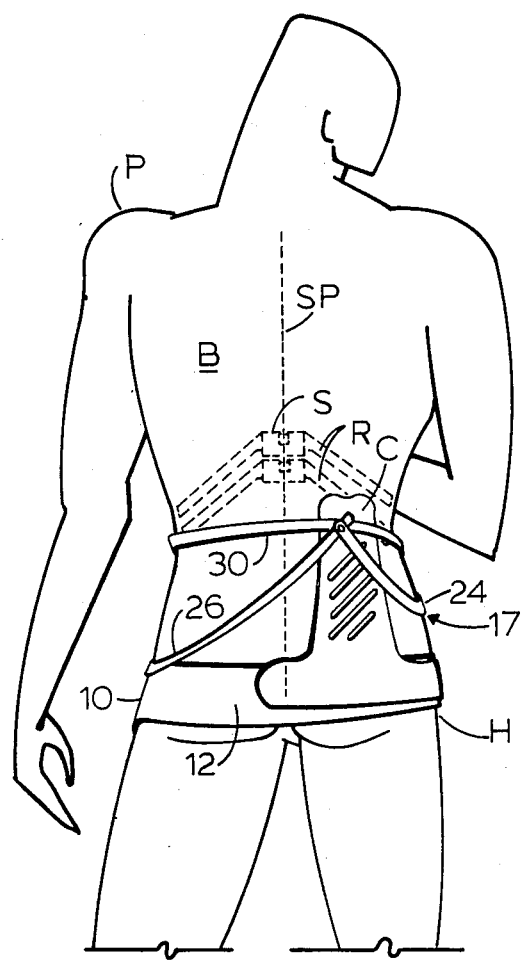
FIG. 2 is a rear view of a patient using the brace of FIG. 1.

Referring to FIGS. 1 and 2, there is shown a patient P wearing a lumbar spinal brace, indicated generally as 10, according to the invention. Patient P has ribs R (shown in phantom), back B, spine S (partially shown in phantom), and sagittal plane SP. For the purpose of describing one embodiment, it is assumed that patient P has suffered a torsional injury in twisting toward his right side. Thus, brace 10 is directed to the problem of preventing further twisting movement toward the right side of patient P.

It will of course be appreciated that a patient could have as easily suffered a torsional injury in twisting toward his left side. In treating such an injury, the principle of the invention is identical. However, the various components of the brace will be located on the opposite side so as to prevent twisting movement toward the left side, rather than to the right.

It is also possible that the user of brace 10 may not have actually injured his spine. For instance, the user may be an industrial worker exposed to torsional stress. In such a case, brace 10 may be worn in order to reduce the risk of torsional injury. In this disclosure, reference to a patient includes a reference to any person, injured or uninjured, who may be using a brace according to the invention.

Figure 3:
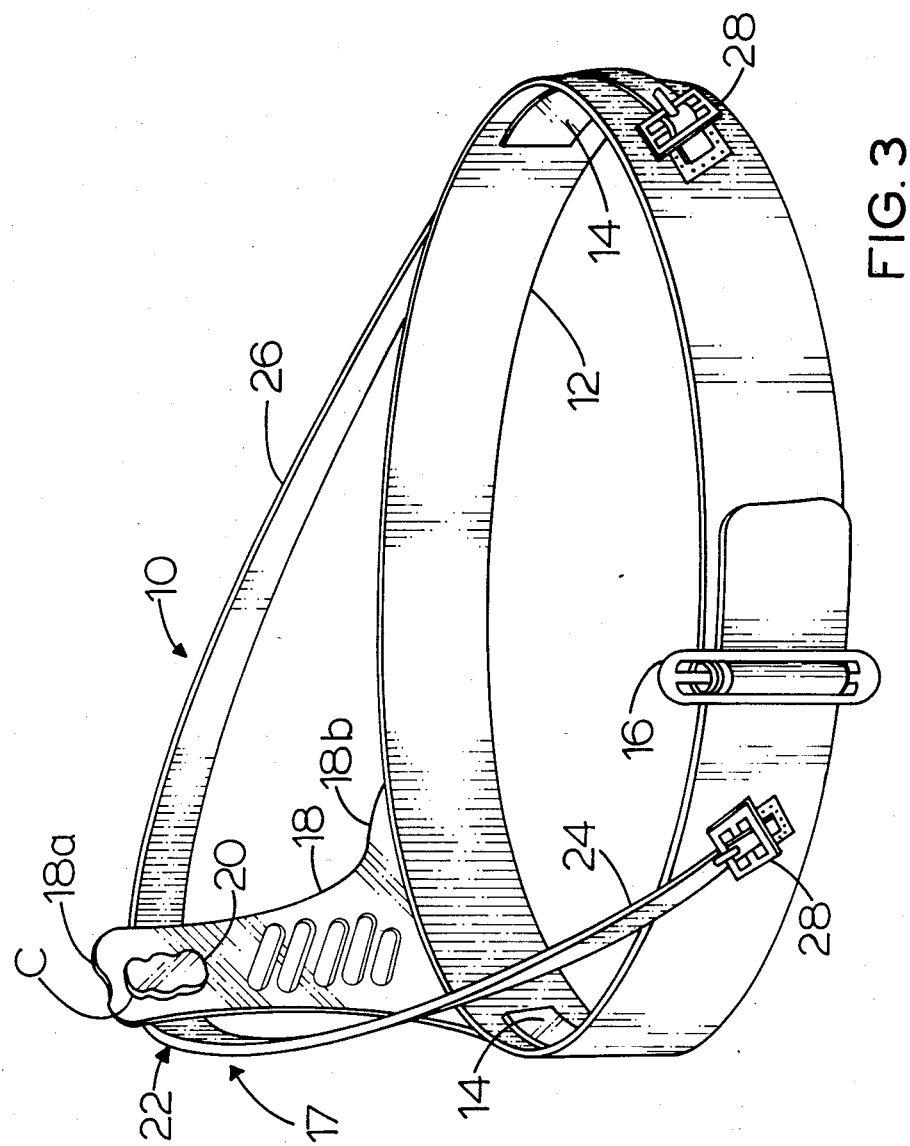
FIG. 3 is a perspective view of a brace according to the invention.

Referring to FIG. 3, brace 10 comprises a belt 12, adaptable to be wrapped around the hips H of patient P (see FIGS. 1 and 2). Belt 12 is sufficiently wide that it is not likely to twist or roll inside-out while it is secured around hips H. Preferably, belt 12 is about three or four inches wide. Belt 12 defines a central axis extending from front to rear.

Frictional pad means 14 may be affixed to belt 12. Such pad means 14 may be permanently secured to belt 12, or they may be adjustably secured for use by different patients. Adjustable pad means 14 require the use of an appropriate fastening means (not shown) for securing the pad means 14 to belt 12.

Belt 12 may be secured about hips H by any suitable and comfortable means, such as by buckle means 16.

A bracing means 17 extends from the belt 12 and defines a contact point C disposed upwardly and laterally from the central axis. The bracing means 17 is resistant to rearward movement of the contact point.

The bracing means 17 comprises a support member 18 extending upwardly from belt 12 adjacent the patient's back B. An upper portion of support member 18 defines contact point C adjacent the lower ribs R. Member 18 preferably does not extend past the lower ribs R because it may interfere with the patient's ability fo flex or extend his spine. Bracing means 17 also comprises a movement limiting means, indicated generally as 22, between support member 18 and belt 12.

Support member 18 is preferably of shape-retaining material and is preferably rigid. Convenient materials are lightweight metal, such as aluminum, or synthetic material, such as plastic or nylon. Other materials may be used. Preferably, support member 18 is pre-formed to fit the contours of the patient's back B. Alternatively, member 18 may be made of a bendable material, which could be shaped to fit the patient's back B when brace 10 is fitted.

Figure 4:
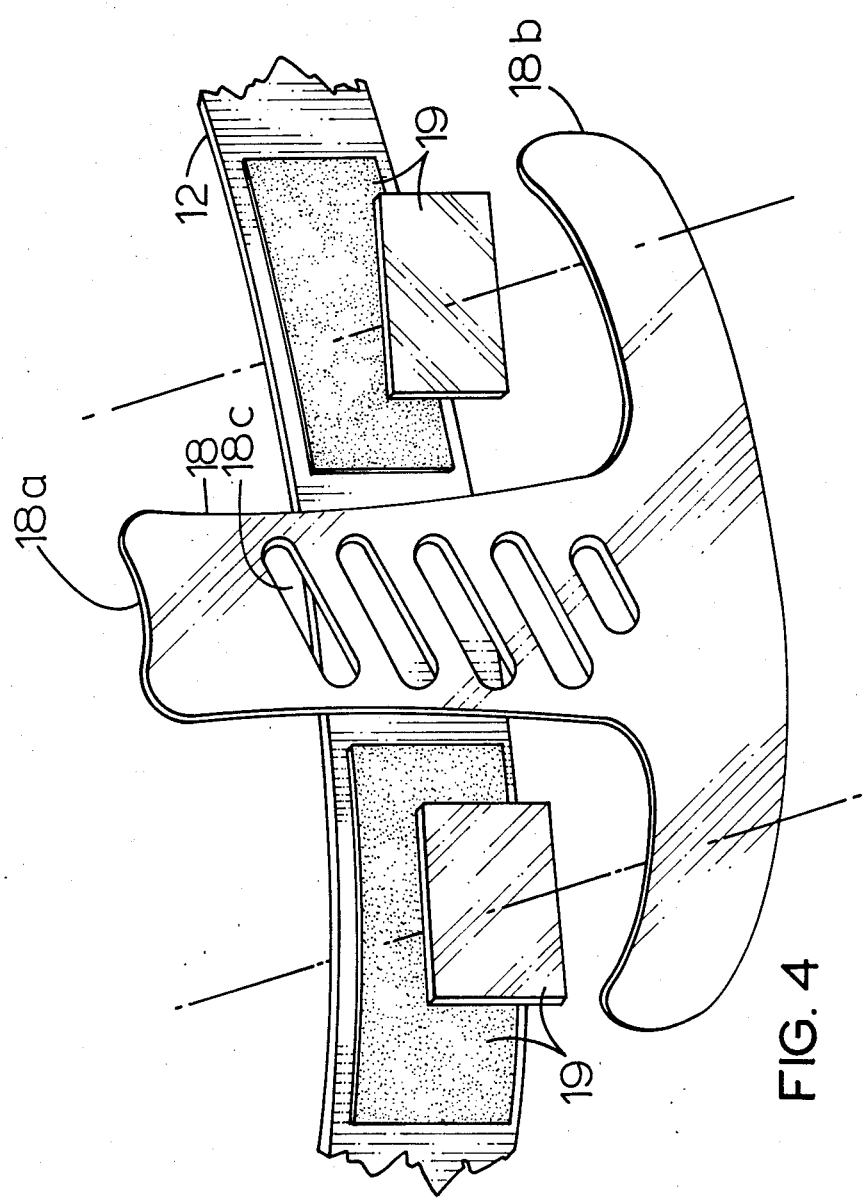
FIG. 4 is an exploded perspective view showing the support member of FIG. 3, and, FIG. 5 is a perspective view of a brace according to an alternate embodiment of the invention.

Support member 18 may be permanently attached at its lower end to belt 12. Preferably, however, member 18 is removeably attached to belt 12, whereby its position on belt 12 may be adjusted for different patients and different injuries. A preferred means 19 (FIG. 4) for removeably attaching member 18 to belt 12 is a loop-and-hook fastener, such as VELCRO (trade mark). A lower end 18b of member 18 may be widened or flared in order to provide a wide base for securing member 18 to belt 12. Support member 18 may have holes or openings 18c to decrease its weight and to improve ventilation. Such openings 18c may be made in any well known manner to optimize the structural strength of member 18.

Support member 18 is preferably disposed laterally away from spine S in order to allow greater mobility in flexion and extension. Contact point C is located a maximum distance away from sagittal plane SP.

A friction pad means 20 may be attached to the upper portion 18a of member 18 at contact point C.

Movement limiting means 22 is attached to upper portion 18a of support member 18. In the illustrated embodiment, movement limiting means comprises a right hand strap 24 extendng from upper portion 18a to a forward position on belt 12 around one side. Similarly, a left hand strap 26 extends from upper portion 18a to a lateral or forward position on belt 12 around the other side. Straps 24 and 26 are sufficiently long so that when patient P is wearing brace 10, straps 24 and 26 will fit snugly and comfortably around his sides. Preferably, straps 24 and 26 are at least one inch wide for the comfort of patient P.

Straps 24 and 26 may be permanently attached at their ends to support member 18 and belt 12. Alternatively, and preferably, for use by different patients with different injuries, straps 24 and 26 are adjustably attached between member 18 and belt 12. In the illustrated embodiment, straps 24 and 26 are attached by buckle means 28 at one end.

For a comfortable fit, belt 12 and straps 24 and 26 may be conveniently made from a flexible, tension-resistant material, such as nylon fabric or plastic strapping.

In operation, friction pad means 14 are located at the appropriate positions on belt 12 for a proper fit on patient P. The shape of support member 18 is checked or adjusted to fit the shape of the patient's back B. Support member 18 is located on belt 12 so that it extends upwardly alongside the patient's back B. Contact point C and friction pad means 20 should be located adjacent the lower ribs R on the side of the injury. Preferably, for maximum leverage, contact point C is located as far as possible from spine S and sagittal plane SP. Conceivably point C could even be located almost at the patient's side. However, support member 18 should not be located so as to interfere with mobility in the uninjured direction. If the torsional injury is toward the patient's right, member 18 is located to the right of spine S. If the injury is to the patient's left, member 18 is offset to the left of spine S.

Belt 12 is fitted and snugly secured around hips H between iliac crest and trochanter, so that rotation of belt 12 around the patient's body is not possible. With patient P in a pre-determined adjustment position, straps 24 and 26 are snugly tightened.

Patient P carries out his normal everyday activities. In any situation where he is required to twist toward the side of his injury, his back B at ribs R will press against friction pad 20 and support member 18. Friction pad means 20 prevents back B from slipping relative to member 18. Pad 20 also provides padding for the added comfort of patient P. If patient P attempts to continue the twist (in the illustrated case toward the right), the upper portion 18a of member 18 will tend to be pushed backward. Strap 24 is placed in tension and resists such backward movement. Belt 12 is unable to rotate under the influence of the force in strap 24, because of friction pads 14 and its snug fit about hips H. Thus, strap 24 resists the further twisting of patient P toward the side of his injury. The resistance in strap 24 also serves to alert patient P to a potentially dangerous activity. Patient P can then act to avoid such dangerous activity. In occupational activities, the brace 10 assists in preventing injury to a worker's spine.

Similarly, because strap 26 may also act to resist backward movement of support member 18, it also resists spinal rotation toward the injured side.

On the other hand, if patient P desires to twist away from the side of the injury, his back B will simply move away from pad 20 and support member 18 without resistance. In addition, patient P is essentially free to flex his spine S. Depending on the patient's initial adjustment position, he may also have substantial freedom to extend his spine S. Thus, his movements (except in the injured direction) may be essentially unimpeded.

It will be appreciated that a brace according to the invention may be made as an unadjustable brace fitted for a single particular person with a particular injury. Alternatively, an adjustable brace may be made, suitable for use by various people with different injuries. In the former case, different left and right hand models in a full range of sizes would have to be available. In the latter case, only a limited range of models would have to be manufactured.

In a further embodiment, a chest strap 30 (see FIGS. 1 and 2) may be attached around the chest of patient P and the upper portion 18a of member 18. Such a strap 30 may offer some resistance to, and hence protection from, injury from, lateral bending away from the side of the injury. Such bending does induce some torsion in the injured direction. Accordingly, in certain situations it may be desireable to reduce or prevent such bending.

It will also be appreciated that in a further embodiment, a brace according to the invention could be used by a patient with torsional injuries in two rotational directions. In such a case, bracing means, support members, movement limiting means, and straps as disclosed herein are attached to the belt on both sides of the spine. In particular, referring to FIG. 5, a first support member 18 and first movement limiting means 17 may be located on one side of the spine and a second support means 118 and second movement limiting means 117 on the other.

In further embodiments, it is possible for braces according to the invention to be made and used with vertebrates other than humans. Such braces may in certain circumstances be of value in veterinary and zoological applications.

The foregoing is a description of a preferred embodiment of the invention which is given here by way of example only. The invention is not to be taken as limited to any of the specific features as described, but comprehends all such variations as come within the scope of the appended claims.

What is claimed is:

1. A lumbar spinal brace comprising:
   a belt adaptable to be wrapped into a generally round shape having left and right hand halves and a central axis dividing said halves;
   a first bracing means extending from the belt;
   a contact point defined by the first bracing means, said contact point being disposed upwardly and laterally from the central axis, the first bracing means being resistant to rearward movement of the contact point; and,
   said first bracing means comprising a support member extending from the belt and having an upper portion defining the contact point, and, a movement limiting means connected to the support member and the belt for resisting rearward movement of the contact point.

2. A lumbar spinal brace as claimed in claim 1 wherein said support member is disposed laterally of the central axis.

3. A lumbar spinal brace as claimed in claim 2 wherein said movement limiting means comprises at least a first strap extending from said upper portion of the support member to a position on the belt on one side of the belt.

4. A lumbar spinal brace as claimed in claim 3 wherein said movement limiting means further comprises a second strap extending from said upper portion of the support member to a position on the belt on the other side of the belt.

5. A lumbar spinal brace as claimed in claim 4 wherein said straps and support member are adjustably secured to the belt.

6. A lumbar spinal brace as claimed in claim 5 including a chest strap means attached to the upper portion of said support member.

7. A lumbar spinal brace to be worn by a user in whom it is desired to resist spinal torsion in at least one rotational direction toward one side of the user, the user defining a sagittal plane, the brace comprising:
   a belt adapted to be secured around the user;
   a first bracing means extending from the belt, and,
   a contact point defined by the first bracing means, said contact point being disposed upwardly from the belt and laterally of the user's sagittal plane, the first bracing means being resistant to rearward movement of the contact point; and,
   said first bracing means comprising a support member extending from the belt alongside the back of the user and having an upper portion defining the contact point adjacent a lower rib on the said side of the user toward which rotation is to be resisted, and, a first movement limiting means connected to the support member and the belt for resisting rearward movement of the contact point during wear by the user.

8. A lumbar spinal brace as claimed in claim 7 wherein said contact point is located adjacent the user's back a maximum distance away from the sagittal plane.

9. A lumbar spinal brace as claimed in claim 8 wherein the support member is disposed laterally of the sagittal plane of the user.

10. A lumbar spinal brace as claimed in claim 9 wherein the belt is a hip belt adapted to be secured around the hips of the user.

11. A lumbar spinal brace as claimed in claim 10 wherein said limiting means comprises at least a first strap extending from the upper portion of the support member to a forward position on the hip belt around said side of the user toward which rotation is to be restricted.

12. A lumbar spinal brace as claimed in claim 11 wherein said limiting means further comprises a second strap extending from the upper portion of the support member to a position on the hip belt around the other side of the user.

13. A lumbar spinal brace as claimed in claim 12 wherein said straps are permanently secured to the support member and to the hip belt and the support member is permanently affixed to the hip belt.

14. A lumbar spinal brace as claimed in claim 12 wherein said straps are adjustably secured between the support member and the hip belt and the support member is adjustably secured to the hip belt.

15. A lumbar spinal brace as claimed in claim 14 wherein the straps are adjustably secured by buckle means.

16. A lumbar spinal brace as claimed in claim 14 wherein the support member is adjustably secured to the hip belt by a loop and hook fastener means.

17. A lumbar spinal brace as claimed in claim 16 wherein the straps are adjustably secured by buckle means.

18. A lumbar spinal brace as claimed in claim 17 including a pad means attached to the upper portion of the support member, the pad means being locatable adjacent the back of the user at his lower ribs at the contact point.

19. A lumbar spinal brace as claimed in claim 18 including frictional pad means on an inner side of the hip belt, said frictional pad means being locatable on each side of the user between his iliac crest and his trochanter.

20. A lumbar spinal brace as claimed in claim 19 wherein said frictional pad means are permanently affixed to the hip belt.

21. A lumbar spinal brace as claimed in claim 19 wherein said frictional pad means are adjustably secured to the hip belt.

22. A lumbar spinal brace as claimed in claim 21 wherein the hip belt includes a belt buckling means, adaptable to secure the hip belt around the hips of the user.

23. A lumbar spinal brace as claimed in claim 11 wherein the support member is wider at its lower end than at its upper end.

24. A lumbar spinal brace as claimed in claim 11 wherein the support member is pre-formed according to the shape of the back of the user.

25. A lumbar spinal brace as claimed in claim 11 wherein the support member is made of a bendable material adaptable to be shaped according to the contours of the back of the user.

26. A lumbar spinal brace as claimed in claim 24 wherein the support member defines openings therethrough.

27. A lumbar spinal brace as claimed in claim 25 wherein the support member defines openings therethrough.

28. A lumbar spinal brace as claimed in claim 11 including a chest strap means, adaptable to be secured around the chest of the user and the upper portion of the support member.

29. A lumbar spinal brace as claimed in claim 7 wherein it is desired to resist rotation in two rotational directions, said support member being a first support member, and said bracing means further comprising a second support member and a second movement limiting means essentially identical to the first support member and first movement limiting means respectively, and located on opposite sides thereto of the hip belt.

30. A lumbar spinal brace as claimed in claim 11 wherein it is desired to resist rotation in two rotational directions, the brace including a second support member and a second movement limiting means essentially identical to the first support member and the first movement limiting means respectively, and located on opposite sides thereto of the hip belt.

31. A lumbar spinal brace as claimed in claim 10 wherein said hip belt is the only means for securing said brace to the user.

* * * * *